United States Patent [19]

Traxler

[11] Patent Number: 4,551,450
[45] Date of Patent: Nov. 5, 1985

[54] RIFAMYCIN HYDRAZONES, PHARMACEUTICAL COMPOSITIONS CONTAINING THEM AND THEIR USE

[75] Inventor: Peter Traxler, Schönenbuch, Switzerland

[73] Assignee: Ciba-Geigy Corporation, Ardsley, N.Y.

[21] Appl. No.: 644,886

[22] Filed: Aug. 27, 1984

[51] Int. Cl.$^4$ .................. A61K 31/395; C07D 519/00
[52] U.S. Cl. .............................. 514/183; 260/239.3 B
[58] Field of Search ................. 260/239.3 P; 514/183

[56] References Cited
U.S. PATENT DOCUMENTS 3,342,810  9/1967  Maggi et al. ................. 260/239.3 B Primary Examiner—Robert T. Bond
Attorney, Agent, or Firm—Michael W. Glynn

[57] ABSTRACT

Novel hydrazones derived from 3-formylrifamycin S or SV as the aldehydo component and a bi- or tri-cyclic N-aminopiperazine as the hydrazino component and having the formula

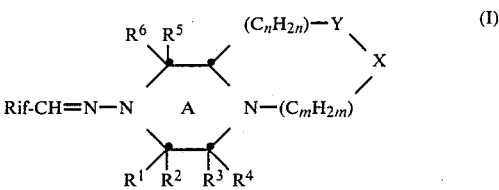

in which
  $R^1$, $R^2$, $R^3$, $R^4$, $R^5$ and $R^6$, independently of one another, each represents a hydrogen atom or $C_{1-4}$-alkyl,
  m and n, independently of one another, each represents an integer from 0 to 5,
  X represents $C_{1-5}$-alkylidene, benzylidene or $C_{1-4}$-alkoxymethylene,
  Y represents $C_{1-5}$-alkylidene, $C_{1-4}$-alkoxymethylene, oxy, thio or optionally substituted imino of the formula —N(R)— wherein R represents hydrogen, $C_{1-4}$-alkyl, $C_{3-5}$-alkenyl, $C_{3-12}$-cycloalkyl or phenyl, or
  X and Y together represent 1,2-cycloalkylene or o-phenylene each of which can be substituted by from one to three $C_{1-4}$-alkyl radicals, and
  Rif represents a radical of rifamycin S or SV that is bonded in the 3-position by the free valency,
are distinguished by a high and long-lasting antituberculotic activity. They are manufactured in conventional manner, for example by condensation of their components.

18 Claims, No Drawings

RIFAMYCIN HYDRAZONES, PHARMACEUTICAL COMPOSITIONS CONTAINING THEM AND THEIR USE

The invention relates to novel polycyclic hydrazones derived from 3-formylrifamycin S or SV as the aldehydro component and a bi- or tri-cyclic N-aminopiperazine as the hydrazino component, especially a 1-aminopiperazine having a 3,4-anellated mono- or bicyclic ring system. The invention relates especially to hydrazones of the formula

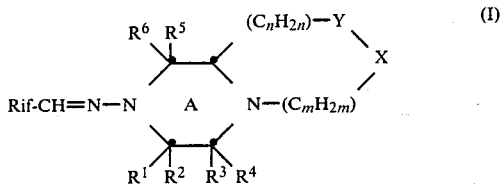

in which

R$^1$, R$^2$, R$^3$, R$^4$, R$^5$ and R$^6$, independently of one another, each represents a hydrogen atom or C$_{1-4}$-alkyl, m and n, independently of one another, each represents an integer from 0 to 5, X represents C$_{1-5}$-alkylidene, benzylidene or C$_{1-4}$-alkoxymethylene, Y represents C$_{1-5}$-alkylidene, C$_{1-4}$-alkoxymethylene, oxy, thio or optionally substituted imino of the formula —N(R)— wherein R represents hydrogen, C$_{1-4}$-alkyl, C$_{3-5}$-alkenyl, C$_{3-12}$-cycloalkyl or phenyl, or X and Y together represent 1,2-cycloalkylene or o-phenylene each of which can be substituted by from one to three C$_{1-4}$-alkyl radicals, and Rif represents a radical of rifamycin S (quinone form) or rifamycin SV (hydroquinone form) that is bonded in the 3-position by the free valency and has the partial formula

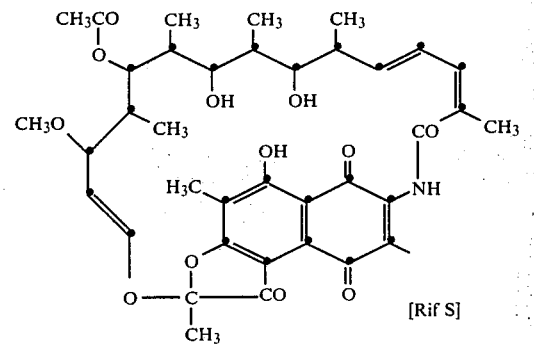

or

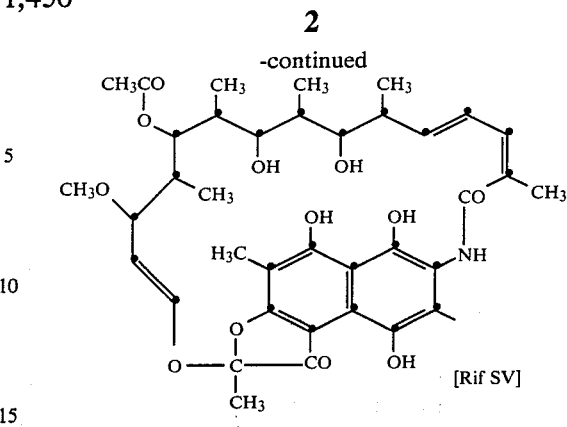

and to salts thereof.

The invention also relates to processes for the manufacture of compounds of the formula I (including their salts), to pharmaceutical compositions containing them and to the manufacture thereof, and to the use of these compounds and pharmaceutical preparations.

In view of the very close relationship between the 1,4-quinone and 1,4-hydroquinone forms (corresponding to rifamycin S and SV, respectively) and the readiness with which the two forms convert into one another, the invention relates in all cases to both forms unless specifically stated otherwise.

C$_{1-4}$-alkyl can be ethyl, propyl and butyl, and also isopropyl, isobutyl, sec.-butyl and tert.-butyl, but preferably methyl. The alkyl radical in C$_{1-4}$-alkoxymethylene has corresponding general and preferred meanings. C$_{3-5}$-alkenyl has an analogous structure with a double bond which is preferably located in the 2- or 3-position; special mention should be made of allyl and methallyl.

C$_{1-5}$-alkylidene is, for example, pentylidene, butylidene, 1-, 2- or 3-methylbutylidene, 1-ethylpropylidene, 1,2-dimethylpropylidene, 1- or 2-methylpropylidene and, preferably, propylidene, isopropylidene, ethylidene and, especially, methylene.

The divalent radicals —C$_m$H$_{2m}$— and —C$_n$H$_{2n}$—, which connect the piperazine ring A with symbols X and Y, respectively, represent a single valency bond (if m or n represents 0), C$_{1-5}$-alkylidene or C$_{2-5}$-alkylene. C$_{1-5}$-alkylidene that separates the piperazine ring A from X or Y by one carbon atom has one of the above-mentioned general or preferred meanings. C$_{2-5}$-alkylene that separates the piperazine ring A from X or Y by from 2 to 5 carbon atoms is derived from a branched or, preferably, straight-chain alkane in which the two free valencies originate from two different carbon atoms situated as desired at the end or in the middle of the chain, and is, for example, pentamethylene, 1- or 2-methyltetramethylene, 1- or 2-ethyltrimethylene, 1,1-, 1,2-, 1,3- or 2,2-dimethyltrimethylene, propylethylene, isopropylethylene, 1-ethyl-(1- or 2-)-methylethylene and 1,1,2-trimethylethylene, and also tetramethylene, 1- or 2-methyltrimethylene, ethylethylene and 1,1- or 1,2-dimethylethylene, and preferably trimethylene, propylene and ethylene. C$_{3-12}$-cycloalkyl is a monovalent mono- or bi-cyclic radical of which the individual rings have from 3 to 8 ring members and can be substituted by from one to four C$_{1-4}$-alkyl radicals, for example those characterised above, but preferably methyl radicals.

There are preferred symmetric combinations of substituents, that is to say those the presence of which does not result in the formation of an asymmetry centre, such as, especially, pairs of the same alkyl radicals situated at one and the same carbon atom (geminal), such as occur, for example, in 4,4-dimethylcyclohexyl or 3,3,4,4-tetramethylcyclopentyl. 1,2-cycloalkylene is a divalent radical analogous to the above-characterised cycloalkyl but is preferably monocyclic and has from 5 to 8 ring members, such as, for example, 1,2-cyclooctylene and 1,2-cyclopentylene, and especially 1,2-cycloheptylene and more especially 1,2-cyclohexylene; the two free valencies have the cis or trans orientation with respect to one another and form the corresponding linkage with ring B. The cycloalkylene radicals can be substituted in a manner analogous to the cycloalkyl radicals, such as, for example, in 4,4-dimethyl-1,2-cyclohexylene or 3,3,5,5-tetramethyl-1,2-cyclopentylene, but unsubstituted radicals are preferred. Phenyl or o-phenylene may also carry from one to four of the above-characterised $C_{1-4}$-alkyl radicals, especially methyl radicals, but are preferably unsubstituted.

The ring B anellated with the piperazine ring A preferably comprises a total of from 5 to 8, especially 5 or 6, and more especially 6, ring members.

Each of the symbols $R^1$ to $R^6$ individually preferably represents hydrogen; if some of them have a meaning other than hydrogen then preferably a maximum of 2 or, more especially, only 1 such radical(s) is involved, methyl being especially preferred. An advantageous arrangement is formed by two identical substituents that are bonded geminally, that is to say at one and the same carbon atom, and therefore do not give rise to an additional asymmetry centre (and, accordingly, to a new pair of diastereoisomers).

Preferred compounds of the formula I are, for example, those in which m represents from 0 to 3 and n represents from 1 to 4, each of the radicals $C_mH_{2m}$ and $C_nH_{2n}$ preferably being straight-chain and/or separating the piperazine ring A from the symbols X and Y, respectively, by a maximum of 3, preferably a maximum of 2, carbon atoms, a maximum of one of the symbols $R^1$ to $R^6$ is other than hydrogen, in which case it represents $C_{1-4}$-alkyl, such as methyl or ethyl, and one of the symbols X and Y represents ethylidene or methylene whilst the other represents $C_{1-4}$-alkylidene, $C_{1-4}$-alkoxymethylene, oxy (—O—), thio (—S—), imino (—NH—), or imino substituted by $C_{1-4}$-alkyl, or X and Y together represent 1,2-cycloalkylene having from 6 to 8 ring atoms or o-phenylene.

Of these, there are more especially preferred, for example, compounds of the formula I in which m represents O and n in a preferably straight-chain radical $C_nH_{2n}$ represents from 1 to 4, a maximum of one of the symbols $R^1$ to $R^6$ is other than hydrogen, in which case it preferably represents methyl, and one of the symbols X and Y represents methylene whilst the other represents ethylidene, propylidene, $C_{1-4}$-alkoxymethylene or, preferably, methylene, or X and Y together represent 1,2-cyclohexylene, 1,2-cycloheptylene, 1,2-cyclooctylene or o-phenylene. Of these, special mention should be made of those in which m represents O, $C_nH_{2n}$ represents methylene, trimethylene or, especially, ethylene, $R^1$ represents methyl or, especially, hydrogen, $R^2$ to $R^6$ each represents hydrogen, X represents ethylidene or, especially, methylene, and Y represents propylidene, isopropylidene, methoxy- or ethoxymethylene, or, especially, methylene, or X and Y together represent 1,2-cyclohexylene or o-phenylene.

Accordingly, there are especially preferred as the hydrazine component N-aminopiperazines having the following basic structure which can be substituted by $C_{1-4}$-alkyl and/or $C_{1-4}$-alkoxy radicals: 3-aminoperhydropyrrolo[1,2-a]pyrazine, 3-aminoperhydro-1H-pyrido-[1,2-a]pyrazine, 3-aminoperhydropyrzino[1,2-a]azepine or 3-aminoperhydro-1H-pyrazino[1,2-a]azocine, or 3-aminoperhydropyrazino[1,2-a]indole, 3-amino-1,2,3,4-4a,5-hexahydropyrazino[1,2-a]indole, 3-aminoperhydro-1H-pyrazino[1,2-a]quinoline, 3-amino-2,3,4,4a,5,6-hexahydro-1H-pyrazino[1,2-a]quinoline.

There are more especially preferred also, for example, those compounds of the formula I in which m and n, independently of one other, each represents from 1 to 3, the radicals $C_mH_{2m}$ and $C_nH_{2n}$ each separating the piperazine ring A from the symbols X and Y, respectively, by a maximum of 2, preferably by 1, carbon atom(s), a maximum of one of the symbols $R^1$ to $R^6$ is other than hydrogen, in which case it preferably represents methyl, and one of the symbols X and Y represents ethylidene or methylene whilst the other represents oxy, thio or imino, it being possible for the imino to be substituted, preferably in the manner indicated above, especially by $C_{1-4}$-alkyl, more especially by isobutyl or methyl. Of these, special mention should be made of those in which m and n each represent 1, $R^1$ represents methyl or, preferably, hydrogen, $R^2$ to $R^6$ each represent hydrogen, X represents methylene and Y represents oxy, thio, imino or $C_{1-4}$-alkylimino, such as, especially, isobutylimino or methylimino. Accordingly there are especially preferred as the hydrazine component especially also N-aminopiperazines having the following basic structure which can be C- and/or N-substituted by $C_{1-4}$-alkyl radicals: 6-aminoperhydropyrazolo[2,1-c]p-oxazine, 6-aminoperhydropyrazolo[2,1-c]p-thiazine, and 3-amino-6-R-perhydro-1H-pyrazino[1,2-a]pyrazine, R in the last name indicating the substituent of the imino group (including hydrogen).

Very especially preferred are all the compounds of the formula I mentioned in the Examples in both forms, that is to say both of the quinone (S) and of the hydroquinone (SV) series, even where only one form is expressly mentioned, and corresponding salts.

Most of the compounds of the formula I may, according to their individual character, also be in the form of salts. Those compounds having sufficient acidity, such as, especially, the hydroquinones of the SV series, can form salts with bases, such as, especially, inorganic bases, preferably physiologically tolerable alkali metal salts, especially sodium and potassium salts. Those compounds of the formula I having sufficient basicity can be in the form of acid addition salts, especially physiologically tolerable salts, with customary pharmaceutically acceptable acids; of the inorganic acids special mention should be made of hydrohalic acids, such as hydrochloric acid, and sulphuric acid and phosphoric or pyrophosphoric acid, and of the organic acids especially the sulphonic acids, for example the aromatic sulphonic acids, such as benzene- or p-toluene-sulphonic acid, embonic acid and sulphanilic acid, or lower alkanesulphonic acids, such as methanesulphonic, ethanesulphonic, hydroxyethanesulphonic and ethylenedisulphonic acid, or alternatively aliphatic, alicyclic, aromatic or heterocyclic carboxylic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic and p-aminosalicylic acid, and also amino acids, especially naturally occurring α-amino acids, such as glycine, leucine, methionine, tryptophan, lysine or arginine, and ascorbic acid. Compounds of the formula I that contain both basic and acidic functional groups may also be in the form of internal salts.

Some hydrazones derived from 3-formylrifamycin SV have already been described. In particular, in U.S. Pat. No. 3,342,810 there are described and claimed, among other antimicrobially active derivatives of the latter-mentioned primary substance, also hydrazones of the partial formula $=N-N(R_2)R_3$ in which $R_2$ and $R_3$, in addition to a number of meanings for each symbol individually, both together and together with the nitrogen atom represent a heterocyclic ring having from 5 to 7 atoms. Apart from this definition in patent claim 6, the description provides no more detailed characterisation of the heterocyclic ring; there are simply listed nine Examples of specific individual compounds (including data relating to their biological action) in the Table, column 3, compounds 3 to 14. Of these, special mention is made later in the text (column 5, lines 64–75, and column 6, lines 30 to 45) of the hydrazone of 3-formylrifamycin SV with 1-amino-4-methylipiperazine because of its excellent antituberculotic activity, and this compound is protected in the specific claim 15. This compound, under the generic name rifampicin, has until now been one of the leading therapeutic agents for combating tuberculosis. Hydrazones having more than one heterocyclic ring have not been considered or indicated.

Although rifampicin can be numbered among the best agents for the treatment of tuberculosis infections, in some cases its relatively short dwell time in the organism is a considerable disadvantage. The preparation of medicaments having an action against tuberculosis infections analogous to that of rifampicin but having a prolonged duration of action is therefore one of the most urgent tasks in this field. Until now it has not been possible to find, even among rifamycin derivatives modified in other ways, some of which exhibit a very good antituberculotic action (in exceptional cases up to three times that of rifampicin), active ingredients that are of equal value or even superior to rifampicin with regard to their long-term action.

It has now been found that the novel compounds according to the present invention are distinguished both by a good antituberculotic activity that is superior to that of rifampicin, especially in vivo, and by a considerably increased dwell time in the organism, as can be demonstrated with reference to the following data.

Legend to Table 1
(1) Hydrazones of 3-formylrifamycin SV; the structure is characterised by the ring system (B) anellated to the piperazine ring (A); (1A)-piperazine ring (A) carries methyl in the 2-position.
(2) Test organism: Mycobacterium tuberculosis TB $H_3R_v$
(3) Minimum inhibitory concentration in a plate test in vitro.
(4) In vivo test (mice); administration p.o.
(5) Half-life period of excretion (in hours).
(6) Highest concentration of the active ingredient in the blood plasma.
(7) Comparison substance: the hydrazone of 3-formylrifamycin SV with 1-amino-4-methylpiperazine.

TABLE I

| Ex. No. | Active ingredient (1) | Antituberculotic action (2) | | Pharmacokinetics | | | |
|---|---|---|---|---|---|---|---|
| | | | | Mice | | Rats | |
| | | (3) MIC μg/ml | (4) ED$_{50}$ mg/kg | (5) t/2 h | (6) C$_{max}$ μg/ml | (5) t/2 h | (6) C$_{max}$ μg/ml |
| 1 | Piperidine | 0.03 | 0.8 | 20 | 27.3 | 17.0 | 24.5 |
| 2 | Pyrrolidine | 0.1 | 2.5 | 9.1 | 57.7 | 13.2 | 11.6 |
| 3 | 6-Methyl-piperidine | 0.4 | 1 | 14 | 22.6 | | |
| 4 | 5-Ethyl-piperidine | | | | | | |
| | Isomer A | 0.01 | 0.8 | 55.1 | 29.5 | | |
| | B | 0.03 | 1 | 44.6 | 26.4 | | |
| 5 | Piperidine; (1A) | | | | | | |
| | Isomer A | 0.2 | 3 | 69.3 | 15 | 58.5 | 19.7 |
| | B | 0.4 | 2 | 66 | 38.8 | 44.7 | 16.4 |
| | C | 0.06 | 3 | 15 | 23.7 | | |
| | D | 0.06 | 3 | 25.1 | 33.6 | | |
| 6 | Perhydro-quinoline | | | | | | |
| | Isomer A | 0.03 | | 33.4 | 56.3 | | |
| | B | 0.007 | | 40.9 | 34 | | |
| 7 | 1,2,3,4-Tetrahydro-quinoline | 0.06 | 4.5 | 32.2 | 24 | | |
| 8 | Thio-morpholine | 0.2 | 8 | 8.9 | 72 | | |
| | N'—methyl-piperazine | 0.1 | | | | | |
| | Rifampicin (7) | 0.03 | 5.9 | 6 | 24.8 | 3.8 | 13.9 |

The novel compounds of the formula I can be manufactured in a manner known per se by means of well-known general processes, for example, as follows: (a) a 3formylrifamycin of the formula

$$Rif-CH=O \qquad (II)$$

in which Rif has the meaning given above, or a functional derivative thereof, is reacted with an N-aminopiperazine of the formula

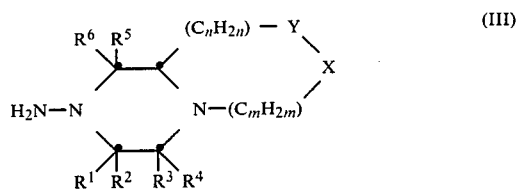

(III)

in which $R^1$ to $R^6$, n, m, X and Y have the meanings given above, or (b) for the direct manufacture of derivatives of the S series, the 3-(rifamycin S)-sulphonic acid of the formula

$$[Rif\ S]-SO_3H \qquad (IV)$$

in which Rif has the meaning given above, is reacted with the formaldehyde hydrazone of an N-aminopiperazine of the formula

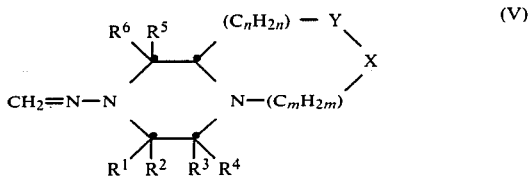 (V)

in which $R^1$ to $R^6$, n, m, X and Y have the meanings given above, and, if desired, when a compound of the formula I in the quinone form is desired, a compound of the formula I present in the hydroquinone form is treated with an oxidising agent, and/or, when a compound of the formula I in the hydroquinone form is desired, a compound of the formula I present in the quinone form is treated with a reducing agent, and/or a compound of the formula I present in free form is converted into a salt thereof, or the compound of the formula I is freed from a salt thereof.

The reaction of a 3-formylrifamycin of the formula II, or of a reactive functional derivative thereof, with the hydrazine of the formula III is effected in a manner known per se, for example in accordance with the above-mentioned U.S. Patent. Especially, the free 3-formylrifamycin SV and the N-aminopiperazine (III) are reacted in approximately equimolar quantities (or with a slight excess of the latter) and preferably in the presence of an organic solvent, such as an alcohol, for example methanol, ethanol or isopropyl alcohol, an open-chain or cyclic ether, for example diethyl ether, 1,2-dimethoxy- or 1,2-diethoxy-ethane, tetrahydrofuran or dioxan, an aliphatic ester or amide, for example ethyl acetate or dimethylformamide, and also dimethyl sulphoxide and acetonitrile, or in a mixture thereof, at temperatures of from approximately −20° to approximately 50° C., preferably between zero and room temperature. The N-aminopiperazine component (III) can also be in the form of an acid addition salt and the base can be freed in situ by the addition of a basic auxiliary, such as an organic alkali metal salt, for example sodium or potassium acetate, or a tertiary organic base, such as a tertiary amine, for example triethylamine, N-methyl- or N-ethyl-piperidine or N-methylmorpholine, or alternatively a heterocyclic aromatic base of the type pyridine and its homologues or quinoline. It is also possible for the aldehyde component of the formula II to be in the form of a functional derivative, for example in the form of an alkali metal salt of the hydroquinone form of the starting material (II), or especially in the form of a reactive derivative with a functionally modified aldehyde group, for example in the form of a compound of the formula Rif—CH=Z (IIA), in which Rif has the meaning given above and is especially [Rif S] and Z represents an oximino, N-substituted imino, unsubstituted or N-(mono- or di-) substituted hydrazono, or semicarbazono group. The substituents of the imino and hydrazono group are monovalent hydrocarbon radicals each having a maximum of 8 carbon atoms, such as, especially, alkyl or cycloalkyl radicals having a maximum of 7 carbon atoms, phenyl or benzyl, or analogous divalent radicals that together with the nitrogen atom form a saturated monocyclic heterocycle having from 5 to 7 ring members and optionally contain in the ring an additional hetero atom, such as oxygen, sulphur (II), nitrogen, or nitrogen mono-substituted by $C_{1-4}$-alkyl. There are preferred those substituents and their combinations which result in readily volatile amines or hydrazines, especially those having a boiling point at normal or reduced temperature of a maximum of 60° C., methyl being especially preferred. When using such a derivative of the aldehyde component (II), the operation is carried out, also in a manner known per se, analogously to the method described above for free aldehyde. If the component (II) is then used in the form of a salt of a base, it is advantageous to adjust the reaction mixture to a neutral reaction, for example by using the other component (the N-aminopiperazine III) in the form of an acid addition salt, or alternatively by the careful addition of an acid, such as a carboxylic acid, for example acetic acid. If the aldehyde component (II) is used in the form of a derivative with a functionally modified aldehyde group, the operation can advantageously be carried out in a relatively large excess of the basic component (III) which then acts simultaneously as solvent. The reaction conditions, especially the temperature and pressure, are so adjusted that the volatile reaction products (for example the amine or hydrazine of the formula $ZH_2$), which are freed from the starting material (II) by the exchange reaction, are removed continuously from the reaction mixture by distillation. Advantageously the pressure is reduced in such a manner that the temperature during distillation does not exceed approximately 60° C. and preferably does not exceed approximately 40° C. Under similar conditions it is also possible, however, to carry out the exchange in an inert organic solvent, such as one of those mentioned above, for example dimethyl sulphoxide.

Process variant (b) is also carried out in a manner known per se. Reactant V is preferably reacted with the 3-[rifamycin S]-sulphonic acid (IV) in a molar ratio of from 1:1 to 5:1, especially of approximately from 1:1 to 2:1, and advantageously in an inert organic solvent, such as one of those mentioned above, preferably a dipolar solvent, for example acetonitrile, dimethylformamide, hexamethylphosphoric acid triamide or, especially, dimethyl sulphoxide, the temperature being from approximately 0° to approximately 70° C., preferably from room temperature to approximately 50° C. The reaction is especially carried out in the presence of an oxidising agent that is suitable for oxidising hydroquinones to quinones, such as, especially, manganese dioxide, the oxidising agent and the hydrazone component (V) being used in an approximately equimolar ratio.

The rifamycin derivatives of the formulae II and IV used as starting materials are known. Compounds of the formulae III and V are also either known or can be obtained by customary standard processes of synthetic organic chemistry. Thus, the bi- or tri-cyclic N-aminopiperazines of the formula III can be obtained, for example, by nitrosation (for example by means of nitrous acid freed in situ or nitrogen dioxide $N_2O_4$) of the corresponding N-unsubstituted bi- or tri-cyclic piperazine of the formula VI defined below and subsequent conventional reduction of the resulting nitrosamine, for example by means of a complex hydride, such as, especially, lithium aluminium hydride, or by catalytic hydrogenation.

Bi- and tri-cyclic piperazines of the formula

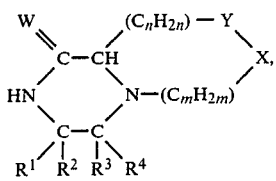

in which R¹ to R⁴, m, n, X and Y have the general or preferred meanings given above and W represents R⁵ and R⁶ having the definition given above, can in turn be obtained, for example, by a simple commonly used synthesis, by condensing a mono- or bi-cyclic nitrogen-containing heterocyclyl-2-carboxylic acid ester of the formula

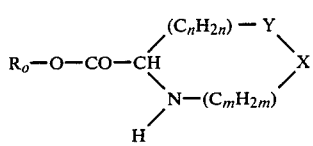

in which $R_o$ represents $C_{1-4}$-alkyl, especially methyl or ethyl, and m, n, X and Y have the meanings given above, with an unsubstituted or substituted ethyleneimine of the formula

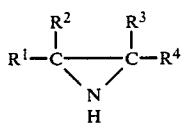

in which R¹ to R⁴ have the meanings given above, and in the resulting piperazone of the formula VI in which R¹ to R⁴, m, n, X and Y have the meanings given above and W represents oxo, converting this oxo group into the substituents R⁵ and R⁶ in conventional manner. If R⁵ and R⁶ each represent hydrogen, this conversion is effected by reduction, for example with diborane or a complex hydride, such as, especially, lithium aluminium hydride. If one or both of the symbols R⁵ and R⁶ represent(s) alkyl, the conversion is effected by treatment with a corresponding organometallic reagent, such as alkyllithium or, especially, an alkylmagnesium halide, for example the chloride or, preferably, bromide, in a suitable inert organic solvent. As is known, the conditions can be so controlled that a "geminal base" having two alkyl substituents, or a mono-alkylated product is obtained; in the latter case, it is necessary for the primary intermediate of the formula VI in which W represents an alkyl together with hydroxy to be reduced further, for example as indicated above for the oxo group. The operation is especially carried out analogously to the reaction conditions given in the following Examples.

Starting materials of the formula V are obtained from the N-aminopiperazines of the formula III with formaldehyde under general conditions that are known for the formation of formaldehyde hydrazones.

In the primary reaction mixture of the process according to the invention, the two oxidation stages of the end product, that is to say the 1,4-quinone form of the S series and the 1,4-hydroquinone form of the SV series, can be present in admixture. Advantageously, however, the whole product is isolated in only one of the two forms, for example in the hydroquinone form. This mixture is advantageously made uniform, as described in more detail below, by forming only the hydroquinone form (derivative of rifamycin SV) by reduction or forming only the quinone form (derivative of rifamycin S) by oxidation.

The conversion according to the invention, if desired, of a quinone of the formula I [Rif S] obtainable according to the process into the corresponding hydroquinone [Rif SV], or of a hydroquinone of the formula I [Rif SV] obtainable according to the process into a quinone [Rif S], or the rendering uniform of a mixture of the two types of compound is effected by means of reduction or oxidation. This conversion can be carried out on a product which has already been isolated or, often more advantageously, before the isolation of the desired product. The reduction can be effected by treatment with a reducing agent, especially a reducing agent that is suitable for reducing a quinone to the corresponding hydroquinone, such as an alkali metal dithionite or hydrosulphite, for example sodium dithionite or hydrosulphite, zinc and acetic acid, or, preferably, with ascorbic acid, and the oxidation can be effected with an oxidising agent, especially with an oxidising agent that is suitable for converting a hydroquinone into the corresponding quinone, such as atmospheric oxygen, hydrogen peroxide, alkali metal ferricyanide, for example potassium ferricyanide, a persulphate salt, for example ammonium persulphate, or manganese dioxide, the oxidation preferably being carried out under basic conditions. The quinones are mostly violet-red coloured compounds, whilst the hydroquinones are usually yellow-coloured and have a better crystallisation ability.

The optional salt-formation, and freeing of the primary forms of the compounds of the formula I from their salts is effected in a conventional manner generally known per se. For example, hydroquinones are converted into the corresponding alkali metal salts by treatment with a corresponding compound having an alkaline reaction, especially a hydroxide, carbonate or bicarbonate; the salts can be converted into free hydroquinone compounds by acidification, for example with inorganic acids, such as, especially, hydrohalic acids. End products of the formula I that have a basic reaction can be converted into their acid addition salts, for example, by treatment with an acid that is suitable for salt-formation, such as one of those mentioned above; conversely, such a basic primary form of a compound of the formula I is freed by treatment with agents having a basic reaction, such as inorganic hydroxides, carbonate and bicarbonates, or organic bases and ion exchangers. Internal salts are formed, for example, by customary acido-basic titration to the neutral point or to the isoelectric point.

The acid addition salts of the novel compounds, such as, for example, the picrates, can also be used for the purification of resulting compounds by converting the free compounds into salts, separating the salts and obtaining the free compounds again from the salts. In view of the close relationship between the compounds in free form and in the form of their salts, hereinbefore and hereinafter the free compounds should be understood as meaning optionally also the corrsponding salts, where appropriate and expedient.

The above-described end products of the formula I, starting materials (III) and (V) and intermediates are optionally obtained as racemates (that is to say mixtures of two antipodes), racemic mixtures (that is to say mixtures of two diastereoisomeric racemates) and diastereoisomeric mixtures (that is to say mixtures of two such diastereoisomers that are not antipodes of one another) and can be separated into the individual antipodes in a manner known per se.

A racemic mixture is produced especially by reaction of a chiral reactant in racemic form with a different chiral reactant that is also in racemic form. If one of the reactants is used in racemic form and the other is used in the form of a single antipode, as is predominantly the case in the process according to the invention, a diastereoisomeric mixture is obtained. Both types of mixture can be separated by physical methods, there being isolated in the former case two racemates and in the latter case two individual diastereoisomers not related to one another. Of the separating methods, special mention should be made of fractional crystallisation, and also various variants of adsorption and partition chromatography, and, in the case of readily volatile mixtures, also fractional distillation and, especially, gas chromatography.

If in the above-described reactions, as is especially the case in the manufacture of starting materials (III) and (V), a racemic starting material is reacted with an achiral reactant, the reaction product is again obtained in the form of a racemate which, as is known, can be separated into the individual antipodes only by using chiral auxiliaries or aids according to methods known per se. A preferred method consists in converting a racemic free base with an optically active acid to form a diastereoisomeric mixture of two acid addition salts, separating this mixture by suitable physical methods, and converting each individual diastereoisomer separately into its components, that is to say the acid and the individual antipode of the base, in a manner known per se, for example by treatment with a relatively strong acid or base. As optically active acids there are suitable, for example, optically active amino acids, especially naturally occurring α-amino acids of the L series and their N-acylated derivatives, the optically active tartaric acids, especially d-tartaric acid and its derivatives with esterified hydroxy groups, d- and l-mandelic acid, d-camphorcarboxylic acid and d- or l-camphor-10-sulphonic acid.

The invention relates also to those forms of the process according to which a compound obtainable as intermediate at any stage of the process is used as starting material and the remaining steps are carried out, or a starting material is used in the form of a derivative, for example a salt, or is formed under the reaction conditions.

In the processes of the present invention it is preferable to use those starting materials which result in the compounds described at the beginning as being especially valuable.

In view of the above-described pharmacological properties of the novel compounds, the present invention also includes the use of the active ingredients according to the invention alone, for example together with adjuncts, or in combination with other active ingredients, especially antibiotics or chemotherapeutics, as agents for the treatment of infections, especially those caused by tubercle bacilli, and by bacteria, especially cocci, such as those mentioned, and both as medicines and as disinfectants. When used as medicines, the active ingredients according to the invention are preferably administered in the form of pharmaceutical preparations together with conventional pharmaceutical carriers or adjuncts. The daily doses to be administered, for example, to warm-blooded animals of approximately 70 kg body weight are, depending upon species, body weight, age and individual condition, and depending upon the mode of administration and, especially, on the sensitivity of the particular causative organism, from approximately 50 to approximately 1000 mg.

The invention also relates to pharmaceutical preparations that contain the compounds of the present invention as active ingredients and to processes for their manufacture.

The pharmaceutical preparations according to the invention are, for example, for enteral, such as peroral or rectal, and for parenteral administration to warm-blooded animals. Suitable dosage unit forms, especially for peroral administration, for example dragées, tablets or capsules, preferably contain from approximately 50 to approximately 500 mg, especially from approximately 100 to approximately 300 mg, of the active ingredient together with pharmaceutically acceptable carriers or adjuncts.

Suitable carriers are, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice and potato starch, gelatine, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores can be provided with suitable coatings that may be resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents or solvent mixtures, or, for the manufacture of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatine, and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

There come into consideration as rectally administrable pharmaceutical preparations, for example, suppositories that consist of a combination of the active ingredient and a suppository base. Suitable as suppository bases are, for example, natural or synthetic triglycerides, paraffin hydrocarbons, polyethylene glycols or higher alkanols. It is also possible to use gelatine rectal capsules that contain a combination of the active ingredient and a base material; suitable base materials are, for example, liquid triglycerides, polyethylene glycols or paraffin hydrocarbons.

Suitable for parenteral administration are especially aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran and optionally also stabilisers. The active ingredient, optionally together with adjuncts, may also be in the form of a lyophilisate and can be made into a solution before parenteral administration by the addition of suitable solvents.

The pharmaceutical preparations of the present invention can be manufactured in a manner known per se, for example by means of conventional mixing, granulating, confectioning, dissolving or lyophilising processes. Thus, pharmaceutical preparations for oral use can be obtained by combining the active ingredient with solid carriers, optionally granulating a resulting mixture, and processing the mixture or granulate, if desired or necessary after the addition of suitable adjuncts, to form tablets or dragée cores.

The following Examples illustrate the invention described above but do not limit the scope thereof in any way. Temperatures are given in degrees Centigrade. Melting points are not corrected. In thin-layer chromatography, silica gel is used as adsorbent and the solvent mixture is given in ratios by volume.

EXAMPLE 1

The hydrazone of 3-formylrifamycin SV with 3-aminoperhydro-1H-pyrido[1,2-a]pyrazine A solution of 1.6 g of 3-aminoperhydro-1H-pyrido[1,2-a]pyrazine in 10 ml of tetrahydrofuran is added to a solution of 5 g of 3-formylrifamycin SV in 100 ml of tetrahydrofuran and the whole is stirred at room temperature for 6 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. Crude hydrazone is obtained which, after crystallization from ethyl acetate, yields orange-red crystals of the title compound which melt, with decomposition, at an undefined temperature. Thin-layer chromatography with methylene chloride/methanol (9:1): $R_f=0.6$; mass spectrum (CDl/CH$_4$, negative): $M^-=862$ (molecular weight calculated for $C_{47}H_{62}N_4O_{12}=862$).

A. The sodium salt of the title compound is obtained by dissolving 3 g of the above free hydrazone in 10 ml of dioxan, adding a solution of 0.929 g of sodium bicarbonate in 10 ml of water and lyophilising the resulting solution.

B. Oxidation to form the quinone:

A solution of 2 g of the hydrazone of 3-formylrifamycin SV with 3-aminoperhydro-1H-pyrido[1,2-a]pyrazine (prepared as described above) in 50 ml of methylene chloride is stirred intensively with pulverulent manganese dioxide for 2 minutes at room temperature; the solid portions are filtered off and the filtrate is concentrated to dryness by evaporation. 2 g of the hydrazone of 3-formylrifamycin S with 3-aminoperhydro-1H-pyrido[1,2-a]pyrazine are obtained in the form of an amorphous blue-black solid having no definite melting point. Molecular weight according to mass spectrum (MH$^+=861$) corresponds to the theoretical value for $C_{46}H_{60}N_4O_{12}$.

The 3-aminoperhydro-1H-pyrido[1,2-a]pyrazine used as starting material can be manufactured as follows:

(a) Nitrosation:

At 5° C., an aqueous solution of 5.86 g of perhydro-1H-pyrido[1,2-a]pyrazine, see M. E. Freed and A. R. Day: J. Org. Chem. 25, 2108 (1960), is adjusted to pH 1.1 with concentrated hydrochloric acid and, while cooling to 0°–5° C., is treated dropwise with a solution of 3.18 g of sodium nitrite in 5 ml of water, stirred for a further two hours at 5°–10° C. and adjusted to pH 13 with approximately 58 ml of an aqueous 2N sodium hydroxide solution. The reaction mixture is extracted with three 80 ml portions of ethyl acetate and the combined organic solutions are dried with sodium sulphate and concentrated by evaporation. The oily residue (6.76 g) is used for the next stage without purification.

(b) Reduction:

A solution of 6.76 g of crude 3-nitrosoperhydro-1H-pyrido[1,2-a]pyrazine (prepared according to stage (a)) in 30 ml of tetrahydrofuran is added dropwise at reflux temperature to a stirred suspension of 1.71 g of lithium aluminium hydride in 150 ml of tetrahydrofuran. The reaction mixture is stirred at room temperature for a further 3 hours; while cooling with ice 10 ml of aqueous 2N sodium hydroxide solution and then 10 ml of water are added and the whole is stirred at room temperature for a further 2 hours. The precipitate is filtered off with suction and then washed on the suction-filter with hot isopropyl alcohol. The filtrate (including the isopropyl alcohol portions) is concentrated by evaporation in vacuo and yields the desired 3-aminoperhydro-1H-pyrido[1,2-a]pyrazine (6.68 g) in the form of a slightly yellow-coloured oil of a purity that is sufficient for the hydrazone formation described above.

EXAMPLE 2

The hydrazone of 3-formylrifamycin SV with 3-aminoperhydropyrrolo[1,2-a]pyrazine A solution of 1.94 g of 3-aminoperhydropyrrolo[1,2-a]pyrazine in 10 ml of tetrahydrofuran is added to a solution of 2 g of 3-formylrifamycin SV in 200 ml of tetrahydrofuran and the whole is stirred at room temperature for 10 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after crystallization from ether, yields orange-red crystals of the title compound, melting point >210° C. with slow decomposition; thin-layer chromatography with methylene chloride/methanol (9:1): $R_f=0.55$; mass spectrum (DCl/CH$_4$, negative): $M^-=848$ (molecular weight calculated for $C_{45}H_{60}N_4O_{12}=848$).

For the manufacture of the 3-aminoperhydropyrrolo[1,2-a]pyrazine used as starting material it is possible, for example, to subject perhydropyrrolo[1,2-a]pyrazine, see M. E. Freed and A. R. Day: J. Org. Chem. 25, 2108 (1960) and R. L. Peck and A. R. Day: J.

Heterocyclic Chem. 6, 181, (1963), to nitrosation and reduction in succession in accordance with Example 1, preparation (a) and (b).

EXAMPLE 3

The hydrazone of 3-formylrifamycin SV with 3-amino-8-methylperhydro-1H-pyrido[1,2-a]pyrazine A solution of 1.86 g of 3-amino-8-methylperhydro-1H-pyrido[1,2-a]pyrazine in 10 ml of tetrahydrofuran is added to a solution of 2 g of 3-formylrifamycin SV in 100 ml of tetrahydrofuran and the whole is stirred at room temperature for 10 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which is separated into two individual stereoisomers by chromatography over silica gel; these stereoisomers are further purified by crystallisation from acetone/ether/hexane.

The two isomers have analogous mass spectra: (FAB, positive): $MH^+ = 877$ (molecular weight calculated for $C_{47}H_{64}N_4O_{12} = 867$).

Isomer A: m.p. 183°–192° C. (decomposition); thin-layer chromatography with methylene chloride/methanol (9:1): $R_f = 0.58$;

Isomer B: m.p. 166°–190° C. (slow decomposition); thin-layer chromatography with methylene chloride/methanol (9:1): $R_f = 0.55$.

For the manufacture of the 3-amino-8-methylperhydro-1H-pyrido[1,2-a]pyrazine used as starting material it is possible, for example, to subject 8-methylperhydro-1H-pyrido[1,2-a]pyrazine to nitrosation and reduction in succession in accordance with Example 1, preparation (a) and (b). The latter compound can be obtained from 2-methyl-6-piperidinecarboxylic acid ethyl ester in accordance with the procedure of Freed and Day, J. Org. Chem. 25, 2108 (1960).

EXAMPLE 4

The hydrazone of 3-formylrifamycin SV with 3-amino-7-ethylperhydro-1H-pyrido[1,2-a]pyrazine A solution of 1.41 g of 3-amino-7-ethylperhydro-1H-pyrido[1,2-a]pyrazine in 10 ml of tetrahydrofuran is added to a solution of 3 g of 3-formylrifamycin SV in 100 ml of tetrahydrofuran and the whole is stirred at room temperature for 20 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which is separated into two amorphous stereoisomers of the title compound by chromatography over 200 g of silica gel. The two isomers produce analogous mass spectra (FAB, negative): $(M-H)^- = 889$ (molecular weight calculated for $C_{48}H_{66}N_4O_{12} = 890$).

Isomer A: m.p. 173°–177° C. (decomposition); thin-layer chromatography with ethyl acetate/cyclohexane (2:1): $R_f = 0.19$;

Isomer B: m.p. 173°–180° C. (decomposition); thin-layer chromatography with ethyl acetate/cyclohexane (2:1): $R_f = 0.31$.

For the manufacture of the 3-amino-7-ethylperhydro-1H-pyrido[1,2-a]pyrazine used as starting material it is possible, for example, to subject 7-ethylperhydro-1H-pyrido[1,2-a]pyrazine to nitrosation and reduction in succession in accordance with Example 1, preparation (a) and (b). The latter compound can be obtained from 3-ethyl-6-piperidinecarboxylic acid ethyl ester in accordance with the procedure of Freed and Day, J. Org. Chem. 25, 2108 (1960).

EXAMPLE 5

The hydrazone of 3-formylrifamycin SV with 3-amino-2-methylperhydro-1H-pyrido[1,2-a]pyrazine A solution of 5.8 g of 3-amino-2-methylperhydro-1H-pyrido[1,2-a]pyrazine in 20 ml of tetrahydrofuran is added to a solution of 20 g of 3-formylrifamycin SV in 500 ml of tetrahydrofuran and the whole is stirred at room temperature for 10 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which is separated into four stereoisomers (A, B, C and D) of the title compound by means of column chromatography over 1.5 kg of silica gel. All the isomers produce an analogous mass spectrum (FAB, negative): $(M-H)^- = 875$ (molecular weight calculated for $C_{47}H_{64}N_4O_{12} = 876$).

The isomers are characterised by the following data; the thin-layer chromatography is carried out with methylene chloride/methanol (9:1) as the solvent system.

|  | | M.p. | $R_f$ |
|---|---|---|---|
| Isomer | A | 176–182° (decomposition) | 0.44 |
|  | B | 172–178° (decomposition) | 0.41 |
|  | C | 155–190° (decomposition) | 0.35 |
|  | D | 170–190° (decomposition) | 0.32 |

The sodium salt of isomer B is formed by adding an aqueous solution of 0.24 g of sodium bicarbonate to a solution of 2.5 g of isomer B and lyophilising the resulting solution.

For the manufacture of the 3-amino-2-methylperhydro-1H-pyrido[1,2-a]pyrazine used as starting material it is possible, for example, to subject 2-methylperhydro-1H-pyrido[1,2-a]pyrazine, see C. Winterfield and G. Gierenz: Chem. Ber. 92, 240 (1959), to nitrosation and reduction in succession in accordance with Example 1, preparation (a) and (b).

EXAMPLE 6

The hydrazone of 3-formylrifamycin SV with 3-aminoperhydro-1H-pyrazino[1,2-a]quinoline A solution of 3.48 g of 3-aminoperhydro-1H-pyrazino[1,2-a]quinoline in 10 ml of tetrahydrofuran is added to a solution of 5 g of 3-formylrifamycin SV in 150 ml of tetrahydrofuran and the whole is stirred at room temperature for 5 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. A crude mixture of four stereoisomeric hydrazones is obtained from which two stereoisomers (A and B) of the title compound are isolated in pure form by column chromatography over 200 g of silica gel. The two isomers produce an analogous mass spectrum (FAB, negative): $(M-H)^- = 915$ (molecular weight calculated for $C_{50}H_{68}N_4O_{12} = 916$).

Isomer A: m.p. 165°–170° C. (decomposition); $R_f = 0.5$

Isomer B: m.p. 168°–180° C. (decomposition); $R_f = 0.42$.

[The thin-layer chromatography is effected with methylene chloride/methanol (9:1) as the solvent system.]

For the manufacture of the 3-aminoperhydro-1H-pyrazino[1,2-a]quinoline used as starting material it is possible, for example, to subject perhydro-1H-pyrazino[1,2-a]quinoline to nitrosation and reduction in succession in accordance with Example 1, preparation (a) and (b). The latter compound can be obtained from 2,3,4,4a,5,6-hexahydro-1H-pyrazino[1,2-a]quinoline, see Swiss Patent Specification No. 498 849, by catalytic hydrogenation on platinum oxide in glacial acetic acid.

EXAMPLE 7

The hydrazone of 3-formylrifamycin SV with 3-amino-2,3,4,4a,5,6-hexahydro-1H-pyrazino[1,2-a]quinoline A solution of 0.57 g of 3-amino-2,3,4,4a,5,6-hexahydro-1H-pyrazino[1,2-a]quinoline in 10 ml of tetrahydrofuran is added to a solution of 2.5 g of 3-formylrifamycin SV in 50 ml of tetrahydrofuran and the whole is stirred at room temperature for 10 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after crystallisation from ether/hexane, yields the crystalline title compound. M.p. 173°–180° C. (decomposition); thin-layer chromatography with methylene chloride/methanol (9:1): $R_f = 0.60$. Mass spectrum (DCI/CH$_4$, negative): $M^- = 910$ (molecular weight calculated for $C_{50}H_{62}N_4O_{12} = 910$).

For the manufacture of the 3-amino-2,3,4,4a,5,6-hexahydro-1H-pyrazino[1,2-a]quinoline used as starting material it is possible, for example, to subject 2,3,4,4a,5,6-hexahydro-1H-pyrazino[1,2-a]quinoline, see Swiss Patent Specification No. 498 849, to nitrosation and reduction in succession in accordance with Example 1, preparation (a) and (b).

EXAMPLE 8

The hydrazone of 3-formylrifamycin SV with 6-aminoperhydropyrazolo[2,1-c]-p-thiazine A solution of 1.0 g of 6-aminoperhydropyrazolo[2,1-c]p-thiazine in 10 ml of tetrahydrofuran is added to a solution of 3 g of 3-formylrifamycin SV in 50 ml of tetrahydrofuran and the whole is stirred at room temperature for 10 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after crystallisation from acetone/ether/hexane, yields the crystalline title compound, m.p. 173°–181° C. (decomposition); $R_f = 0.71$ [thin-layer chromatography with methylene chloride/methanol (9:1)]. Mass spectrum (FAB, negative): $(M-H)^- = 879$ (molecular weight calculated for $C_{45}H_{60}N_4O_{12}S = 880$).

For the manufacture of the 6-aminoperhydropyrazolo[2,1-c]p-thiazine used as starting material it is possible, for example, to subject perhydropyrazolo[2,1-c]p-thiazine to nitrosation and reduction in succession in accordance with Example 1, preparation (a) and (b). The latter compound can be obtained from thiomorpholine-2-carboxylic acid ethyl ester in accordance with the procedure of Freed and Day, J. Org. Chem. 25, 2108 (1960).

EXAMPLE 9

The hydrazone of 3-formylrifamycin SV with 3-amino-6-methylperhydro-1H-pyrazino[1,2-a]pyrazine A solution of 2.04 g of 3-amino-6-methylperhydro-1H-pyrazino[1,2-a]pyrazine in 10 ml of tetrahydrofuran is added to a solution of 3 g of 3-formylrifamycin SV in 100 ml of tetrahydrofuran and the whole is stirred at room temperature for 15 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after crystallisation from acetone/ether, yields a crystalline mixture of two stereoisomers of the title compound, which mixture has a melting point of 170° C. (decomposition) and in thin-layer chromatography with methylene chloride/methanol (9:1) produces two products with $R_{fA} = 0.47$ and $R_{fB} = 0.41$. Mass spectrum (FAB, negative): $(M-H)^- = 876$ (molecular weight calculated for $C_{46}H_{63}N_5O_{12} = 877$).

For the manufacture of the 3-amino-6-methylperhydro-1H-pyrazino[1,2-a]pyrazine used as starting material it is possible, for example, to subject 6-methylperhydro-1H-pyrazino[1,2-a]pyrazine, see H. J. Beim and A. R. Day: J. Heterocyclic Chem. 14, 307 (1977), to nitrosation and reduction in succession in accordance with Example 1, preparation (a) and (b).

EXAMPLE 10

The hydrazone of 3-formylrifamycin SV with 3-amino-6-isobutylperhydro-1H-pyrazino[1,2-a]pyrazine A solution of 1.73 g of 3-amino-6-isobutylperhydro-1H-pyrazino[1,2-a]pyrazine in 10 ml of tetrahydrofuran is added to a solution of 3 g of 3-formylrifamycin SV in 100 ml of tetrahydrofuran and the whole is stirred at room temperature for 60 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after column chromatography over 200 g of silica gel, yields purified title compound, m.p. 163°–170° C. (decomposition): $R_f = 0.42$ [thin-layer chromatography in methylene chloride/methanol (9:1)]. Mass spectrum (FAB, negative):

$(M-H)^- = 918$ (molecular weight calculated for $C_{49}H_{69}N_5O_{12} = 919$).

For the manufacture of the 3-amino-6-isobutylperhydro-1H-pyrazino[1,2-a]pyrazine used as starting material it is possible, for example, to subject 6-isobutylperhydro-1H-pyrazino[1,2-a]pyrazine, prepared in accordance with H. J. Beim and A. R. Day: J. Heterocyclic Chem. 14, 307 (1977), to nitrosation and reduction in succession in accordance with Example 1, preparation (a) and (b).

EXAMPLE 11

The hydrazone of 3-formylrifamycin SV with 3-amino-6-cyclopentylperhydro-1H-pyrazino[1,2-a]pyrazine A solution of 1.8 g of 3-amino-6-cyclopentylperhydro-1H-pyrazino[1,2-a]pyrazine in 10 ml of tetrahydrofuran is added to a solution of 3 g of 3-formylrifamycin SV in 50 ml of tetrahydrofuran and the whole is stirred at room temperature for 15 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after chromatography over 200 g of silica gel, yields the title compound. Mass spectrum (FAB, negative): $(M-H)^- = 930$ (molecular weight calculated for $C_{50}H_{69}N_5O_{12} = 931$).

For the manufacture of the 3-amino-6-cyclopentylperhydro-1H-pyrazino[1,2-a]pyrazine used as starting material it is possible, for example, to subject 6-cyclopentylperhydro-1H-pyrazino[1,2-a]pyrazine, prepared according to H. J. Beim and A. R. Day: J. Heterocyclic Chem. 14, 307 (1977), to nitrosation and reduction in succession in accordance with Example 1, preparation (a) and (b).

EXAMPLE 12

The hydrazone of 3-formylrifamycin SV with 6-aminoperhydropyrazino[2,1-c]-p-oxazine A solution of 1.94 g of 6-aminoperhydropyrazino[2,1-c]p-oxazine in 10 ml of tetrahydrofuran is added to a solution of 3 g of 3-formylrifamycin SV in 100 ml of tetrahydrofuran and the whole is stirred at room temperature for 100 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after crystallisation from ethyl acetate/cyclohexane, yields orange-red crystals of the title compound. Mass spectrum (FAB, negative): $(M-H)^- = 863$ (molecular weight calculated for $C_{45}H_{60}N_4O_{13} = 864$).

For the manufacture of the 6-aminoperhydropyrazino[2,1-c]p-oxazine used as starting material it is possible, for example, to subject perhydropyrazino[2,1-c]p-oxazine to nitrosation and reduction in succession in accordance with Example 1, preparation (a) and (b). The latter compound can be obtained from morpholino-2-carboxylic acid ethyl ester in accordance with the procedure of Freed and Day, J. Org. Chem. 25, 2108 (1960).

EXAMPLE 13

The hydrazone of 3-formylrifamycin SV with 3-amino-7-methoxyperhydro-1H-pyrido[1,2-a]pyrazine A solution of 1.37 g of 3-amino-7-methoxyperhydro-1H-pyrido[1,2-a]pyrazine in 10 ml of tetrahydrofuran is added to a solution of 3 g of 3-formylrifamycin SV in 100 ml of tetrahydrofuran and the whole is stirred at room temperature for 60 minutes until according to thin-layer chromatography all the 3-formylrifamycin SV has been consumed. For working up, the reaction solution is concentrated in vacuo and the residue is taken up in methylene chloride. The organic phase is washed twice with dilute aqueous citric acid solution, dried and concentrated by evaporation. The crude hydrazone is obtained which, after column chromatography over 200 g of silica gel, yields purified title compound. Mass spectrum (FAB, negative): $(M-H)^- = 891$ (molecular weight calculated for $C_{47}H_{64}N_4O_{13} = 892$).

For the manufacture of the 3-amino-7-methoxyperhydro-1H-pyrido[1,2-a]pyrazine used as starting material it is possible, for example, to subject 7-methoxyperhydro-1H-pyrido[1,2-a]pyrazine to nitrosation and reduction in succession in accordance with Example 1, preparation (a) and (b). The latter compound can be obtained from 2-methoxy-6-piperidinecarboxylic acid ethyl ester in accordance with the procedure of Freed and Day, J. Org. Chem. 25, 2108 (1960).

EXAMPLE 14

Capsules, each containing 250 mg of the hydrazone of 3-formylrifamycin SV with 3-aminoperhydro-1H-pyrido[1,2-a]pyrazine, can be manufactured as follows:

Composition (for 1000 capsules):

| | |
|---|---|
| hydrazone of 3-formylrifamycin SV with 3-aminoperhydro-1H—pyrido-[1,2-a]pyrazine | 250.0 g |
| corn starch | 50.0 g |
| polyvinylpyrrolidone | 15.0 g |
| magnesium stearate | 5.0 g |
| ethanol | q.s. |

The active ingredient and the corn starch are mixed together and moistened with a solution of the polyvinylpyrrolidone in 50 g of ethanol. The moist mass is pressed through a sieve of 3 mm mesh width and dried at 45° C. The dry granulate is passed through a sieve of 1 mm mesh width and mixed with 5 g of magnesium stearate. 0.320 g portions of the mixture are introduced into dry-fill capsules, size 0.

Capsules containing a dose, having an equivalent action, of each individual product from Examples 2 to 13 are manufactured in analogous manner.

I claim:

1. A compound of the formula

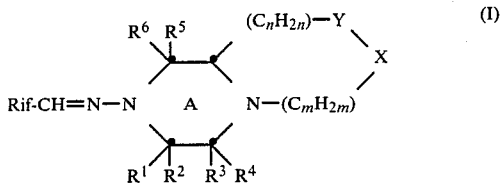

in which p1 R¹, R², R³, R⁴, R⁵ and R⁶, independently of one another, each represents a hydrogen atom or $C_{1-4}$-alkyl, m and n, independently of one another, each represents an integer from 0 to 5, X represents $C_{1-5}$-alkylidene, benzylidene or $C_{1-4}$-alkoxymethylene, Y represents $C_{1-5}$-alkylidene, $C_{1-4}$-alkoxymethylene, oxy, thio or optionally substituted imino of the formula —N(R)— wherein R represents hydrogen, $C_{1-4}$-alkyl, $C_{3-5}$-alkenyl, $C_{3-12}$-cycloalkyl or phenyl, or X and Y together represent 1,2-cycloalkylene or o-phenylene each of which can be substituted by from one to three $C_{1-4}$-alkyl radicals, and Rif represents a radical of the partial formula

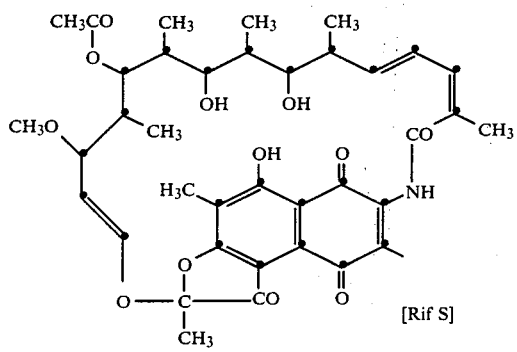

or

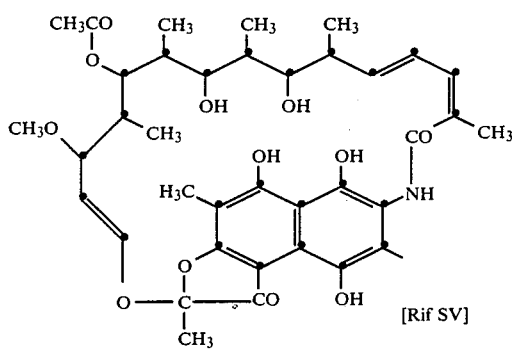

and salts thereof.

2. A compound according to claim 1 in which m represents from 0 to 3 and n represents from 1 to 4, each of the radicals $C_mH_{2m}$ and $C_nH_{2n}$ separating the piperazine ring A from the symbols X and Y, respectively, by a maximum of 3 carbon atoms, a maximum of one of the symbols R¹ to R⁶ is other than hydrogen, in which case it represents methyl or ethyl, and one of the symbols X and Y represents ethylidene or methylene whilst the other represents $C_{1-4}$-alkylidene, $C_{1-4}$-alkoxymethylene, oxy (—O—), thio (—S—), imino (—NH—), or imino substituted by $C_{1-4}$-alkyl, or X and Y together represent 1,2-cycloalkylene having from 6 to 8 ring atoms or o-phenylene.

3. A compound according to claim 1 in which m represents O and n in a straight-chain radical $C_nH_{2n}$ represents from 1 to 4, a maximum of one of the symbols R¹ to R⁶ is other than hydrogen, in which case it represents methyl, and one of the symbols X and Y represents methylene whilst the other represents ethylidene, propylidene, $C_{1-4}$-alkoxymethylene or methylene, or X and Y together represent 1,2-cyclohexylene or o-phenylene.

4. A compound according to claim 1 in which m and n, independently of one other, each represents from 1 to 3, the radicals $C_mH_{2m}$ and $C_nH_{2n}$ each separating the piperazine ring A from the symbols X and Y, respectively, by 1 carbon atom, a maximum of one of the symbols R¹ to R⁶ is other than hydrogen, in which case it represents methyl, and one of the symbols X and Y represents ethylidene or methylene whilst the other represents oxy, thio or imino, it being possible for the imino to be substituted by $C_{1-4}$-alkyl, $C_{5-8}$-cycloalkyl or phenyl.

5. A compound according to claim 1 that is the hydrazone of 3-formylrifamycin SV or S with 3-aminoperhydro-1H-pyrido[1,2-a]pyrazine.

6. A compound according to claim 1 that is the hydrazone of 3-formylrifamycin SV or S with 3-aminoperhydropyrrolo[1,2-a]pyrazine.

7. A compound according to claim 1 that is the hydrazone of 3-formylrifamycin SV or S with 3-amino-8-methylperhydro-1H-pyrido[1,2-a]pyrazine.

8. A compound according to claim 1 that is the hydrazone of 3-formylrifamycin SV or S with 3-amino-7-ethylperhydro-1H-pyrido[1,2-a]pyrazine.

9. A compound according to claim 1 that is the hydrazone of 3-formylrifamycin SV or S with 3-amino-2-methylperhydro-1H-pyrido[1,2-a]pyrazine.

10. A compound according to claim 1 that is the hydrazone of 3-formylrifamycin SV or S with 3-aminoperhydro-1H-pyrazino[1,2-a]quinoline.

11. A compound according to claim 1 that is the hydrazone of 3-formylrifamycin SV or S with 3-amino-2,3,4,4a,5,6-hexahydro-1H-pyrazino[1,2-a]quinoline.

12. A compound according to claim 1 that is the hydrazone of 3-formylrifamycin SV or S with 6-aminoperhydropyrazolo[2,1-c]p-thiazine.

13. A compound according to claim 1 that is the hydrazone of 3-formylrifamycin SV or S with 3-amino-6-R-perhydro-1H-pyrazino[1,2-a]pyrazine in which R represents methyl, isobutyl or cyclopentyl.

14. A compound according to claim 1 that is the hydrazone of 3-formylrifamycin SV or S with 6-aminoperhydropyrazolo[2,1-c]p-oxazine.

15. A compound according to claim 1 that is the hydrazone of 3-formylrifamycin SV or S with 3-amino-7-methoxyperhydro-1H-pyrido[1,2-a]pyrazine.

16. A compound according to claim 1 that is derived from rifamycin SV, or a pharmaceutically acceptable alkali metal salt thereof.

17. A pharmaceutical composition useful for the treatment of infections of the human or animal body containing an effective antimicrobially active amount of a compound of formula I defined in claim 1 (or a pharmaceutically acceptable salt thereof) together with a suitable carrier.

18. A method for the treatment of infections in the human or animal body, characterised by the administration to the affected subject of an antimicrobially active dose of one of the compounds of of the formula I defined in claim 1, or a pharmacologically acceptable salt thereof, alone or together with a suitable carrier.

* * * * *

UNITED STATES PATENT AND TRADEMARK OFFICE
CERTIFICATE OF CORRECTION

PATENT NO. : 4,551,450

DATED : November 5, 1985

INVENTOR(S) : Peter Traxler

It is certified that error appears in the above-identified patent and that said Letters Patent is hereby corrected as shown below:

Last page:, Column 21, line 10 reads as follows:

[in which p1, $R^1$, $R^2$, $R^3$, $R^4$, $R^5$ and $R^6$, independently of] this should be deleted and it should read correctly as follows:

-- in which $R^1$, $R^2$, $R^3$, $R^4$, $R^5$ and $R^6$, independently of --

*Signed and Sealed this*

*Fourteenth* Day of *January 1986*

[SEAL]

Attest:

Attesting Officer

DONALD J. QUIGG

Commissioner of Patents and Trademarks